US00PP18707P2

(12) United States Plant Patent
Meilland

(10) Patent No.: US PP18,707 P2
(45) Date of Patent: Apr. 1, 2008

(54) GRANDIFLORA ROSE PLANT NAMED 'MEILUDERE'

(50) Latin Name: *Rosa hybrida*
Varietal Denomination: cv. Meiludere

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/634,930

(22) Filed: Dec. 7, 2006

(51) Int. Cl.
*A01A 5/00* (2006.01)

(52) U.S. Cl. ..... Plt./137
(58) Field of Classification Search ..... Plt./137
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct variety of Grandiflora rose plant is provided that abundantly forms on a nearly continuous basis attractive pink blossoms. A bushy growth habit is displayed and the medium green foliage is semi-glossy. The plant develops well on its own roots in alkaline soil. The disease tolerance is good particularly with respect to Botrytis. The plant is well suited for providing attractive ornamentation in parks and gardens.

1 Drawing Sheet

Figures 1, 2, 3, 4, 5, 6, 7, 8, 9, 10, 11, 12, 13, 14, 15, 16, 17, 18:
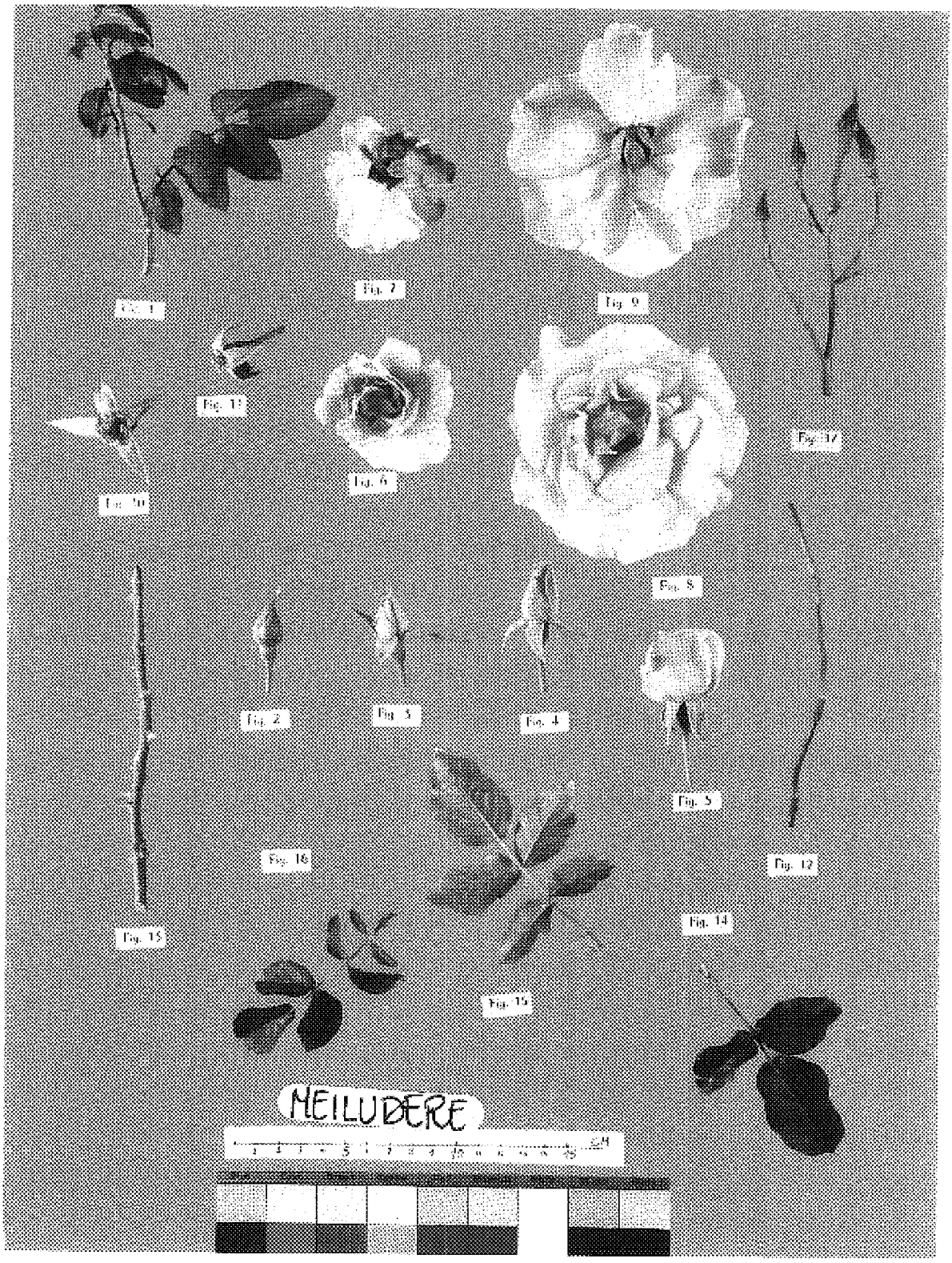

Botanical/commercial classification: *Rosa hybrida*/Grandiflora Rose Plant.
Varietal denomination: cv. Meiludere.

SUMMARY OF THE INVENTION

The new variety of *Rosa hybrida* Grandiflora rose plant was created by artificial pollination wherein two parents were crossed which previously had been studied in the hope that they would contribute the desired characteristics. The female parent (i.e., the seed parent) was the product of the cross of the 'Paloma Blanca' variety (U.S. Plant Pat. No. 2,853) and the 'Bucbi' variety (U.S. Plant Pat. No. 4,225). The 'Bucbi' variety sometimes is known as the 'Carefree Beauty' variety. The male parent (i.e., the pollen parent) was the product of the cross of the 'Meituraphar' variety (non-patented in the United States) and the 'Meicloux' variety (non-patented in the United States). The 'Meituraphar' variety sometimes is known as the 'Anne de Bretagne' variety.

(*'Paloma Blanca'*×*'Bucbi'*)×(*'Meituraphar'*×*'Meicloux'*).

The seeds resulting from the above pollination were sown and small plants were obtained which were physically and biologically different from each other. Selective study resulted in the identification of a single plant of the new variety.

It was found that the new Grandiflora rose plant of the present invention:

(a) exhibits a bushy growth habit, (b) forms in abundance on a nearly continuous basis attractive pink blossoms, (c) displays semi-glossy medium green foliage, (d) exhibits good tolerance to diseases particularly with respect to Botrytis, (e) develops well on its own roots in alkaline soil, and (f) is particularly well suited for growing as attractive ornamentation in the landscape.

The new variety well meets the needs of the horticultural industry and can be grown to advantage as attractive ornamentation in parks and gardens.

The new variety can be readily distinguished from its ancestors. For instance, the blossom coloration is considerably different from that of the 'Paloma Blanca,' 'Meituraphar' and 'Meicloux' varieties. More specially, the 'Paloma Blanca' variety forms white blossoms, the 'Meituraphar' variety forms deeper pink blossoms, and 'Meicloux' variety forms yellow blended with orange blossoms. The blossoms of the new variety possess more petals than those of the 'Bucbi' variety and the growth habit is more erect than that of the 'Bucbi' variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meiludere'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one-and-one-half year of age and were observed during October while growing on their own roots outdoors at Le Cannet des Maures, Var, France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface; and FIG. 16 — illustrates a specimen of a leaf with seven leaflets — plan view — upper surface; and FIG. 17 — illustrates a cluster of unopened floral buds.

DETAILED DESCRIPTION

The chart used in the identification of the colors is that of The Royal Horticultural Society (R.H.S. Colour Chart). The description is based on the observation of one-and-one-half-year-old plants during October while growing on their own roots outdoors at Le Cannet des Maures, Var, France.

Class: Grandiflora.

Plant:

*Height.*—Approximately 110 to 130 cm on average at the end of the growing season.

*Width.*—Approximately 80 to 90 cm on average at the end of the growing season.

*Habit.*—Bushy.

Branches:

*Color.*—Young stems: near Yellow-Green Group 146B. Adult wood: near Yellow-Green Group 146A.

*Thorns.*—On young stems: small prickles: quantity: none. Long prickles: configuration: elongated and curved downwards on the upper surface, concave on the under surface, and with an oboval and long base. Quantity: approximately 3 on average on a stem length of 10 cm. Length: ≧0.8 cm. Color: near Red Group 53B. On adult stems: Small prickles: quantity: none. Long prickles: configuration: elongated and curved downwards on the upper surface, concave on the under surface, and with an oboval and long base. Quantity: approximately 3 on average on a stem length of 10 cm. Length: ≧0.8 mm. Color: near Greyed-Orange Group 166A.

Leaves:

*Stipules.*—Smooth texture, adnate, pectinate and rather broad.

*Petioles.*—Upper surface: near Green Group 143C and Yellow-Green Group 144D in coloration. Under surface: near Yellow-Green Group 144A in coloration. Length: approximately 2.5 cm for the terminal leaflet.

*Rachis.*—Upper surface: near Yellow-Green Group 144A in coloration. Under surface: near Yellow-Green Group 144A in coloration.

*Leaflets.*—Number: 3, 5 (mostly often), and 7. Shape: generally elliptical with a cuspidate tip and an obtuse base. Size: the terminal leaflets commonly are approximately 7 cm in length and approximately 3.5 cm in width on average. Serration: small and single (as illustrated). Texture: physically firm and thick. General appearance: dense, medium green, and semi-glossy. Color (young foliage): upper surface: near Green Group 143B. Under surface: near Green Group 143C. Color (adult foliage): upper surface: near Green Group 137A. Under surface: near Green Group 138B.

Inflorescence:

*Number of flowers.*—Commonly one to four blossoms per stem.

*Peduncle.*—Smooth, approximately 6 cm in length on average, approximately 0.3 cm in diameter on average, and near Yellow-Green Group 144B in coloration.

*Sepals.*—Upper surface: tomentose and near Yellow-Green Group 148D in coloration. Under surface: smooth and near Green Group 143C in coloration. Size: near 3 cm in length on average, and near 0.7 cm in width at the widest point on average.

*Buds.*—Shape: conical. Size: medium. Length: approximately 1.5 cm on average. Width: near 1 cm on average at the widest point. Color: Upper surface: near Orange Group 27D to Red Group 36C. Under surface: near Red Group 49C and 49D.

*Flower.*—Shape: cup-shaped. Diameter: approximately 11 cm on average. Color (in the course of opening): upper surface: near Red Group 36C. Under surface: near Red Group 49C and near Yellow Group 2C towards the base. Basal petal spot: near Yellow Group 2C on the upper surface. Color (when fully open): upper surface: near Red Group 36C. Under surface: near Red Group 49C and near Yellow Group 2C towards the base. Basal petal spot: near Yellow Group 2C on the upper surface. Color stability: substantially no discoloration with age. Fragrance: none. Lasting quality: the blossoms commonly last approximately 12 days on the plant on average, and approximately 8 days on average when cut and placed in a vase. Petal number: approximately 35 on average under normal growing conditions. Petal shape: cuneiform base with a substantially rounded tip. Petal texture: consistent and somewhat firm. Petal base: cuneiform. Petal length: approximately 4 cm on average. Petal width: approximately 4 cm on average. Petal arrangement: imbricated; and without petaloids. Petal drop: good with the petals commonly detaching cleanly. Stamen number: approximately 70 to 75 on average. Anthers: regularly arranged around the styles, approximately 0.2 cm in size on average, and near Yellow Group 13C in coloration. Pollen: present and near Yellow Group 3C in coloration. Filaments: approximately 0.4 cm in length on average and near Yellow Group 3D in coloration. Pistils: approximately 60 to 65 on average. Stigmas: approximately 0.5 cm in size on average and near Yellow-Green Group 147D in coloration. Styles:

approximately 0.3 cm in length on average, and near Yellow-Green Group 147D in coloration. Receptacle: smooth, pitcher-shaped in longitudinal section, approximately 0.9 cm in length on average, approximately 0.8 cm in width on average at the widest point, and near Yellow-Green Group 144B in coloration. Hips: none observed during observations to date.

Development:

*Vegetation.*—Very strong.

*Blooming.*—Early, very abundant, and nearly continuous.

*Tolerance to diseases.*—Good, particularly with respect to Botrytis.

*Aptitude to bear fruit.*—None observed.

I claim:

1. A new and distinct Grandiflora rose plant characterized by the following characteristics:

(a) exhibits a bushy growth habit, (b) forms in abundance on a nearly continuous basis attractive pink blossoms, (c) displays semi-glossy medium green foliage, (d) exhibits good tolerance to diseases particularly with respect to Botrytis, (e) develops well on its own roots in alkaline soil, and (f) is particularly well suited for growing as attractive ornamentation in the landscape;

substantially as herein shown and described.

* * * * *

MEILUDERE